United States Patent [19]

Yoon

[11] Patent Number: 5,478,318
[45] Date of Patent: Dec. 26, 1995

[54] MULTILUMINAL ENDOSCOPIC PORTAL

[76] Inventor: InBae Yoon, 2101 Highland Ridge Dr., Phoenix, Md. 21131

[21] Appl. No.: 285,636

[22] Filed: Aug. 2, 1994

Related U.S. Application Data

[63] Continuation-in-part of Ser. No. 557,869, Jul. 26, 1990, Pat. No. 5,395,342.

[51] Int. Cl.$^6$ .................................................. A61M 39/06
[52] U.S. Cl. .................................... 604/167; 604/169
[58] Field of Search ...................... 604/167, 256, 604/169, 248

[56] References Cited

U.S. PATENT DOCUMENTS

| | | |
|---|---|---|
| 3,747,812 | 7/1973 | Karmen et al. . |
| 3,788,318 | 1/1974 | Kim et al. . |
| 3,833,003 | 9/1974 | Tarico . |
| 4,126,133 | 11/1978 | Schwartz ................................ 604/169 |
| 4,187,849 | 2/1980 | Stim . |
| 4,524,770 | 6/1985 | Orandi . |
| 4,535,773 | 8/1985 | Yoon . |
| 4,601,710 | 7/1986 | Moll . |
| 4,654,030 | 3/1987 | Moll et al. . |
| 4,668,221 | 5/1987 | Luther . |
| 4,689,047 | 8/1987 | Bauer ................................ 604/169 |
| 4,735,614 | 4/1988 | Yapp et al. . |
| 4,769,005 | 9/1988 | Ginsburg et al. . |
| 4,790,817 | 12/1988 | Luther . |
| 4,808,168 | 2/1989 | Warring . |
| 4,902,280 | 2/1990 | Lander . |
| 4,931,042 | 6/1990 | Holmes et al. . |
| 4,942,280 | 7/1990 | Lander . |
| 5,030,206 | 7/1991 | Lander . |
| 5,053,016 | 10/1991 | Lander . |
| 5,389,080 | 2/1995 | Yoon ........................................ 604/167 |
| 5,395,342 | 3/1995 | Yoon ........................................ 604/167 |

FOREIGN PATENT DOCUMENTS 10244100  3/1966  United Kingdom .

*Primary Examiner*—Paul J. Hirsch

[57] ABSTRACT

An endoscopic portal includes a tubular sleeve or cannula having an open distal end for positioning within an anatomical cavity, an open proximal end for positioning externally of the anatomical cavity, and a valve assembly disposed at the open proximal end of the sleeve for controlling fluid passing therethrough. The valve assembly includes a spherical valve body defining a plurality of different size lumens or passages that can be selectively aligned with the open proximal end of the sleeve. The valve body is rotatably carried in a valve housing mounting the proximal end of the sleeve and is preferably biased toward a position closing a passage formed through the valve housing.

14 Claims, 3 Drawing Sheets

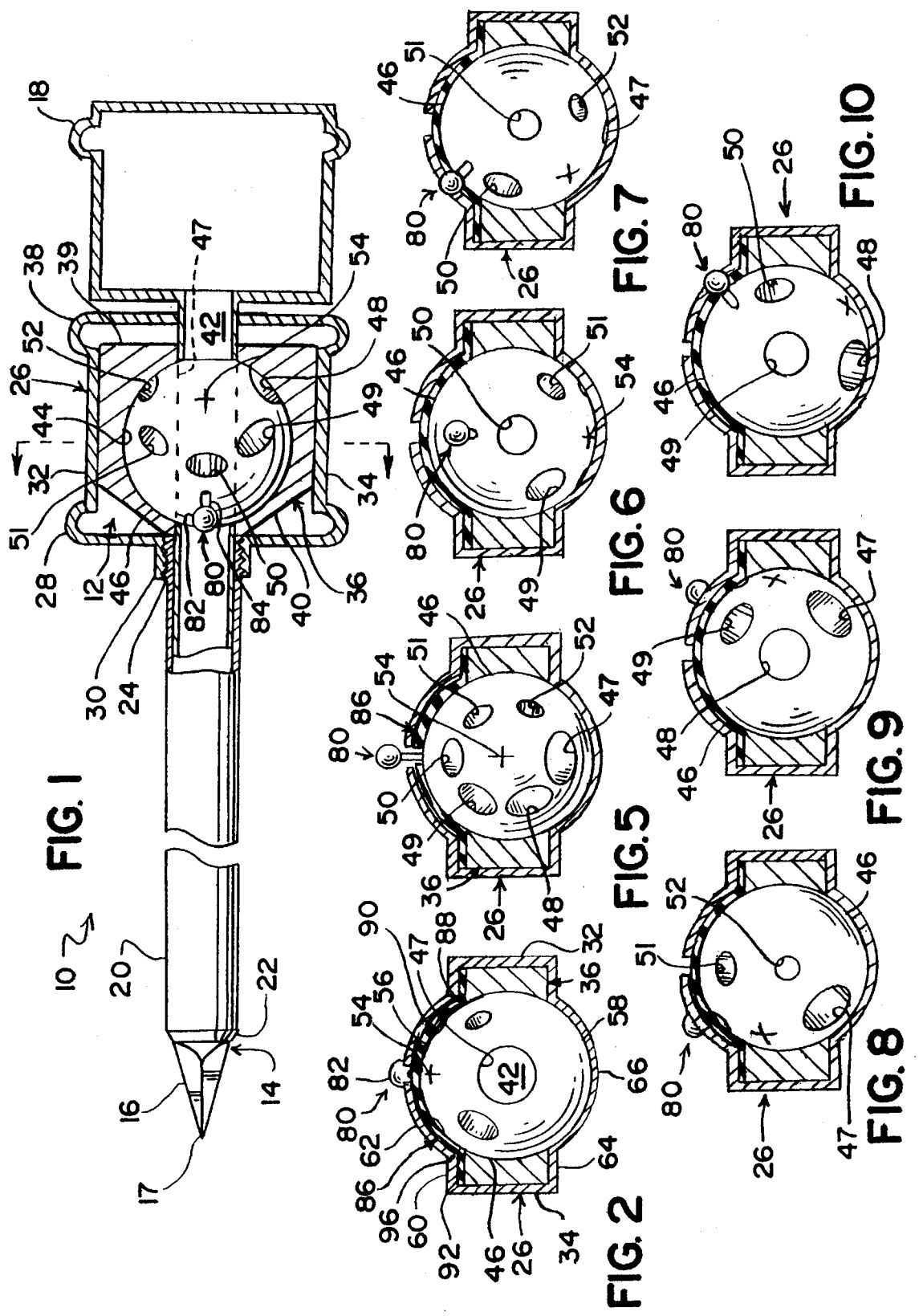

20
MULTILUMINAL ENDOSCOPIC PORTAL

CROSS-REFERENCE TO RELATED APPLICATIONS

This application is a continuation-in-part of prior application Ser. No. 07/557,869, filed Jul. 26, 1990, now U.S. Pat. No. 5,395,342 the disclosure which is incorporated herein by reference.

BACKGROUND OF THE INVENTION

1. Field of the Invention

The present invention pertains to medical instruments and, more particularly, to a valve assembly for providing a variable size passage in an endoscopic portal to prevent fluid through the portal while allowing implements of various sizes to be selectively introduced through the valve.

2. Description of the Prior Art

Medical procedures involving the placement of an endoscopic portal, such as a sleeve or cannula, through an anatomical cavity wall to provide a passage for insertion of medical instruments frequently required that the passage be sealed to prevent the flow of fluids through the endoscopic portal. For example, many medical procedures gain access to an anatomical cavity by utilizing a penetrating member, such as a trocar, obturator or needle, having a sharp penetrating tip for puncturing the cavity wall to establish communication with the interior of the anatomical cavity. A sleeve or cannula is then left in situ for utilization as a portal to introduce medical instruments into the anatomical cavity. Because it is necessary to prevent fluid flow to and from the site within the anatomical cavity, the portal must be sealed prior to and subsequent to the introduction of any instruments and while such instruments are in place. Furthermore, fluids, such as gaseous phase carbon dioxide or nitrous oxide, may be introduced into the anatomical cavity for insufflation as part of the procedure, and the escape of the gas must be prevented during penetration and during the endoscopic procedure. Typically, medical instruments are inserted into the portal via a valve that has a single, particular size passage dependent upon the penetrating member. However, additional instruments to be introduced into the anatomical cavity through the passage may be of diverse types and sizes and it will be appreciated that fluid can escape past smaller instruments.

A penetrating member is usually received within a portal sleeve that passes through the wall of an anatomical cavity with the penetrating member and remains in place to establish communication with the interior of the cavity after the penetrating member has been removed from the sleeve. The sleeve typically has a proximal end secured in a housing provided with a valve that allows the penetrating member to be inserted into the sleeve. The valve prevents the flow of fluids to and from the anatomical cavity and closes when the penetrating member is removed from the sleeve. The size of the penetrating member utilized varies depending upon the procedure and the type of anatomical cavity to be penetrated. Once the penetrating member has been removed from the sleeve, a great variety of instruments of various sizes and diameters are introduced into the anatomical cavity via the portal dependent upon the procedure to be performed.

Prior art endoscopic portals utilize a valve, such as a flapper or gate valve, that is normally biased to a closed position but in an open position has a passage or lumen therethrough of only a single size. Accordingly, such endoscopic portals suffer from the disadvantages of allowing the passage or leakage of fluids when surgical instruments smaller than the single passage are introduced therethrough or of limiting the implements to be used in a procedure to a single size. Additionally, such endoscopic portals can be effectively used with only a single size penetrating member.

SUMMARY OF THE INVENTION

Accordingly, it is a primary object of the present invention to overcome the above described disadvantages of the prior art by utilizing a valve assembly in an endoscopic portal that provides a variable size passage therethrough to engage medical instruments of various sizes in sealing relation.

Another object of the present invention is to define multiple lumens or passages of diverse sizes in a valve assembly for an endoscopic portal to selectively produce a sealing relation with medical instruments of various sizes.

A further object of the present invention is to utilize a valve assembly to normally seal an opening or passage through an endoscopic portal and to permit medical instruments of diverse sizes to be introduced through the opening or passage while preventing fluid flow or leakage.

The present invention has another object in the use of a spherical valve body to define multiple lumens or passages of diverse sizes in an endoscopic portal for selectively producing a sealing relation with medical instruments of various sizes.

Some of the advantages of the present invention over the prior art are that a complete endoscopic procedure can be performed with a single portal thereby reducing instrument costs and surgery time, a single endoscopic portal can be used with various sizes and types of penetrating members, and the endoscopic portal can be inexpensively manufactured to be economically disposable for single patient use.

The present invention is generally characterized in an endoscopic portal including a tubular sleeve or cannula having an open distal end for positioning within an anatomical cavity, an open proximal end for positioning externally of the anatomical cavity, and a valve assembly disposed at the open proximal end of the sleeve for controlling fluid passing therethrough. The valve assembly includes a spherical valve body defining a plurality of different size lumens or passages that can be selectively aligned with the open proximal end of the sleeve. The valve body is rotatably carried in a valve housing mounting the proximal end of the sleeve and is preferably biased toward a position closing a passage formed through the valve housing.

Another aspect of the present invention is generally characterized in a method of forming a portal in the wall of an anatomical cavity by selectively rotating a spherical valve body within a valve housing to align a first passage formed in the valve body with the open proximal end of a portal sleeve mounting the valve housing, inserting a penetrating member through the passage and sleeve, penetrating the anatomical cavity wall with the penetrating member and portal sleeve, withdrawing the penetrating member from the sleeve, selectively rotating the valve body to align a second passage formed in the valve body with the open proximal end of the portal sleeve, and inserting a medical instrument through the valve body and sleeve to access a site within the anatomical cavity.

Other objects and advantages of the present invention will become apparent from the following description of the preferred embodiments taken in conjunction with the accompanying drawings wherein, unless specified otherwise, like parts or parts that perform like functions are identified in each of several figures by the same reference characters.

BRIEF DESCRIPTION OF THE DRAWINGS

FIG. 1 is a top view, partly in section, of an endoscopic portal according to the present invention.

FIG. 2 is a partial sectional view taken along line 2—2 of FIG. 1.

FIGS. 5–10 are partial sectional views taken along line 2—2 in FIG. 1 and illustrating various valve positions.

DESCRIPTION OF THE PREFERRED EMBODIMENTS

Figure 3:
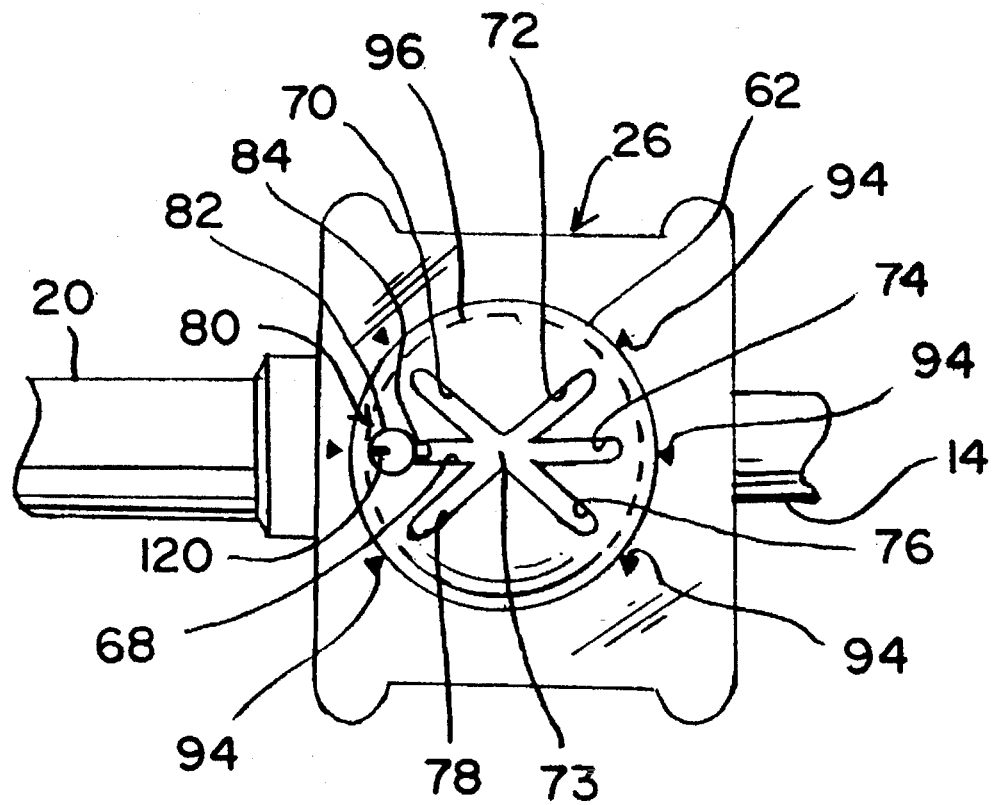
FIG. 3 is a broken top view of the endoscopic portal of FIG. 1.

The endoscopic portal of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the endoscopic portal of the present invention can be used for introduction into anatomical cavities of needles with fluid flow therethrough and catheters as well as for other instruments engaging tissue during surgical or diagnostic procedures. Accordingly, the cannula or outer tubular member of the endoscopic portal can be a portal sleeve, a needle, a catheter or a tubular component of a medical instrument.

With reference to FIG. 1, an endoscopic portal 10 including a valve assembly 12 according to the present invention is shown in combination with a penetrating member 14 for puncturing the wall of an anatomical cavity. The penetrating member 14 is illustrated as a solid trocar having a distal end 16 tapering to a sharp, tissue penetrating tip 17; however, any type of penetrating member can be utilized in combination with the endoscopic portal 10, such as solid obturators or hollow or tubular needles having angled, sharp distal ends. The penetrating member 14 has a proximal end 18 defining an enlarged handle or hub to allow the penetrating member to be withdrawn after insertion of the endoscopic portal 10 into an anatomical cavity.

The endoscopic portal 10 includes a tubular, cylindrical sleeve or cannula 20 for positioning through the anatomical cavity wall during the penetration to provide access to a site within the anatomical cavity. The sleeve 20 has a tapered, open distal end 22 adapted to be disposed within the anatomical cavity and an open proximal end 24 adapted to be disposed externally of the body. The proximal end 24 is externally threaded to engage internal threads at the forward end of a housing 26 to couple the housing with the proximal end of the sleeve. Housing 26 has an enlarged forward flange 28 joined to a tubular end 30 that is internally threaded for receiving the proximal end 24 of sleeve 20. A pair of spaced, parallel side walls 32 and 34 extend from forward flange 28 and connect with an enlarged rear flange 38. A valve block 36 is received within the housing 26 and is closely fitted between side walls 32 and 34. Block 36 includes a proximal face 39 parallel to rear flange 38 and a tapered distal face 40 positioned adjacent tubular end 30.

A longitudinal passage 42 is defined through the housing including an opening in flange 38 and a bore through block 36 in longitudinal alignment with the longitudinal axis of sleeve 20, and implements such as penetrating member 14 can be inserted into the sleeve 20 via the passage 42. A spheroidal cavity 44 is formed in block 36 and centered along the longitudinal axis of the sleeve 20 and the passage 42. A spherical valve body 46 is disposed in cavity 44 and is freely rotatable about a plurality of axes.

A plurality of different size passages or lumens 47, 48, 49, 50, 51 and 52 are formed in valve body 46 diametrically with respect to the center of the valve body. Lumens 47, 48, 49, 50, 51 and 52 have longitudinal axes contained in a plurality of planes intersecting the center of the valve body 46. The lumens 47, 48, 49, 50, 51 and 52 are angularly spaced from each other and form a generally ring-shaped configuration of openings on the surface of the valve body 46. The spacing between lumens 47, 48, 49, 50, 51 and 52 is selected to provide a solid surface 54 on the valve body large enough in size to cover and seal passage 42 when the solid surface 54 is aligned with passage 42 by rotation of the valve body. Lumens 47, 48, 49, 50, 51 and 52 are of different size or diameter; and, as shown, lumen 47 is the largest diameter passage, lumen 48 is the next largest diameter passage, and so on, with lumen 52 being the smallest diameter passage.

Figure 4:
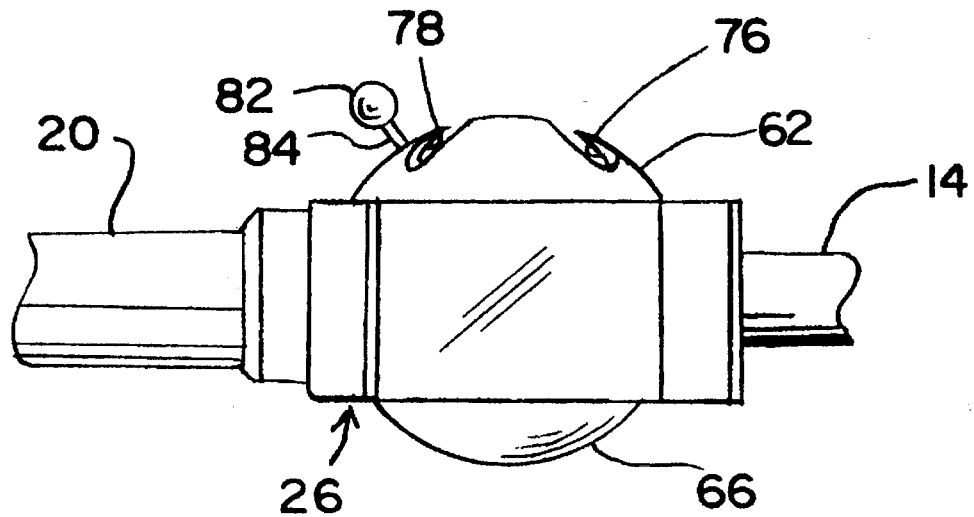
FIG. 4 is a broken side view of the endoscopic portal of FIG. 1.

As depicted in FIG. 2, valve block 36 surrounds only a central portion of valve body 46 so that upper and lower portions 56 and 58 of the valve body 46 project out of the valve block 36. Housing 26 includes a top wall 60 connecting the side walls 32 and 34 and the forward and rear flanges 28 and 38 of the housing and forming a hemispherical dome 62 spaced radially from the protruding upper portion 56 of the valve body 46 to define a small gap therebetween. A bottom wall 64 connects between side walls 32 and 34 and forward and rear flanges 28 and 38 to form a lower hemispherical dome 66 sealingly engaging the lower protruding portion 58 of the valve body 46. As best seen in FIGS. 3 and 4, a plurality of slotted openings 68, 70, 72, 74, 76 and 78 corresponding in number to the number of lumens or passages formed in the valve body 46, are formed in the upper hemispherical dome 62 and extend radially from a common center 73. A handle 80 including a knob 82 mounted on a shaft 84 secured to the valve body 46 extends through the slotted openings 68, 70, 72, 74, 76 and 78 and is movable along the slotted openings to rotate the valve body 46 to a number of predetermined locations for aligning different luminal passages with the longitudinal passage 42. A bias element 86, shown as an elastic membrane 88 in FIG. 2, disposed in the gap between the valve body upper portion 56 and the hemispherical dome 62, biases the valve body 46 to a closed position wherein the solid surface 54 covers the longitudinal passage 42, while permitting rotation of the valve body 46 away from the closed position. The elastic membrane 88 is formed of rubber, or any other resilient material, and includes a generally hemispherical portion 90 surrounding the shaft 84 and a peripheral lip or rim 92 secured between the valve block 36 and the top wall 60 of the housing 26.

In operation, bias element 86 rotationally biases valve body 46 to the closed position shown in FIG. 5 where solid surface 54 blocks or covers the longitudinal passage 42 and handle 80 is disposed at the center 73 of the slotted openings. Valve body 46 may be rotated by grasping the handle 80 and moving the handle along one of the slotted openings 68, 70, 72, 74, 76 or 78 to align the central longitudinal axis of a selected one of the lumens 47, 48, 49, 50, 51 or 52, respectively, with the longitudinal axis of passage 42. With handle 80 positioned at the terminal end of one of the slotted openings, an implement such as penetrating member 14 having a size corresponding to the size of the aligned lumen can be inserted into the opening in flange 38 to extend through the aligned lumen of the valve body and sleeve 20. Since the aligned lumen corresponds to the size of the inserted implement and the valve body 46 is sealingly received in block 36, the passage of fluids through the housing and valve assembly is prevented. The valve assembly therefore, permits diverse surgical instruments to be inserted into the sleeve with a single portal in a manner maintaining a sealed environment.

When utilized in conjunction with penetrating member 14, handle 80 is grasped and moved along slotted opening 68 to rotate valve body 46 into the position shown in FIGS. 1 and 2 to align lumen 47 corresponding in size and cross-sectional shape with penetrating member 14 to provide sealing engagement therebetween. The distal end 16 of penetrating member 14 is inserted into the housing 26 through the opening in flange 38 to extend through passage 42, lumen 47 and sleeve 20 such that distal end 16 projects from the distal end 22 of the sleeve. For laparoscopy, in many cases, a pneumoperitoneum will have been created, for example with the use of a Varres needle. When a solid penetrating member, such as the trocar shown, is forced through the anatomical cavity wall, the penetrating member will function as an obturator and escape of gas from the peritoneum will be prevented due to the seal between the penetrating member and the valve assembly. When the penetrating member is hollow, such as a needle, the proximal end 18 will be closed to prevent passage of fluid therethrough. If no pneumoperitoneum has been created prior to insertion of the penetrating member, insufflation can be accomplished via a valve, not shown, in the proximal end of the needle 18.

Once the anatomical cavity is insufflated and the endoscopic portal is in place with sleeve 20 passing through the anatomical cavity wall, the penetrating member is removed whereupon the bias element 86 automatically restores the valve body to the closed position shown in FIG. 5 to prevent gas from escaping. Valve body 46 can now be rotated using handle 80 to align the same or a different lumen with passage 42 to allow the same or a different sized medical instrument to be inserted therethrough for introduction via the sleeve to the site within the anatomical cavity. More particularly, if handle 80 is moved to a terminal end of slotted opening 74, valve body 46 will assume the position shown in FIG. 6, and lumen 50 will be aligned with passage 42; if handle 80 is moved to a terminal end of slotted opening 76, valve body 46 will assume the position shown in FIG. 7, and lumen 51 will be aligned with passage 42; if handle 80 is moved to a terminal end of slotted opening 78, valve body 46 will assume the position shown in FIG. 8, and lumen 52 will be aligned with passage 42; if handle 80 is moved to a terminal end of slotted opening 70, valve body will assume the position shown in FIG. 9, and lumen 48 will be aligned with passage 42; and, if handle 80 is moved to a terminal end of slotted opening 72, valve body 46 will assume the position shown in FIG. 10, and lumen 49 will be aligned with passage 42.

By use of indicia 94 on the housing wall 60 in combination with handle 80, which can act as a pointer or indicator, accurate alignment of the lumen with passage 42 through the valve assembly, housing and sleeve can further be assured. Consequently, hemispherical dome 62 of housing wall 60 can be removed as indicated by phantom line in FIGS. 2 and 3, leaving an opening 96 through which elastic membrane 88 protrudes, and alignment of the lumen with the passage through the valve assembly can be confirmed solely by reference to the position of handle 80 relative to indicia 94.

Figure 11:
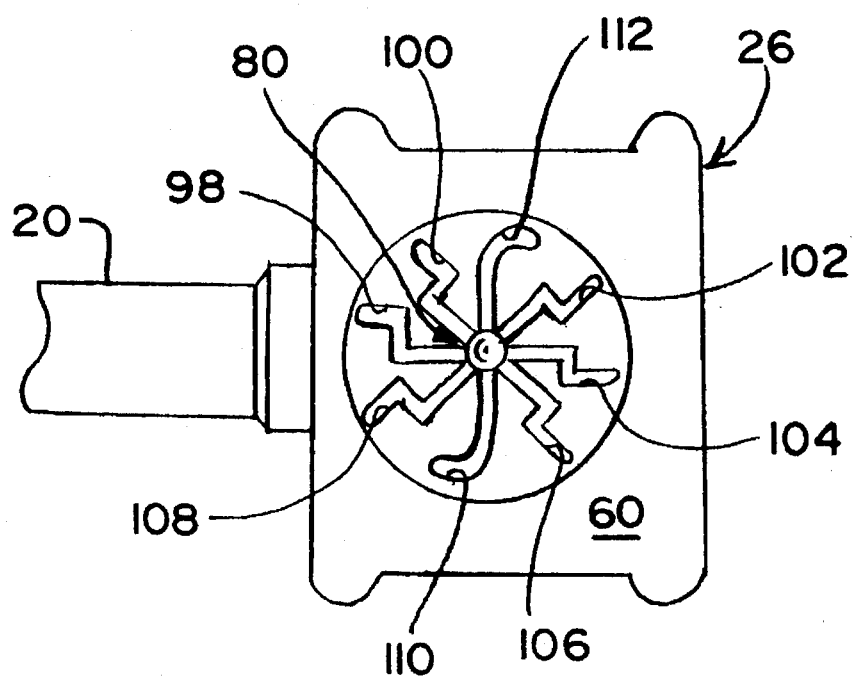
FIG. 11 is a broken top view of another endoscopic portal according to the present invention.

The number of different size lumens or passages in the valve assembly and the sizes thereof are dependent upon the instruments to be used in the endoscopic procedure to be performed and the diameter of the valve body. For example, frequently used instruments commonly have diameters ranging in size from 1 mm to 20 mm in 1 mm increments; and, thus, lumens corresponding to these diameters are preferred. Although six lumens have been illustrated as being formed in valve body 46, it will be appreciated that fewer or more lumens could be formed depending on the relative sizes of the valve body and the lumens, and that the slotted openings would then be configured accordingly to permit rotation of the valve body to align those lumens with the longitudinal passage 42. For example, in FIG. 11, a modification of the endoscopic portal of the present invention is illustrated wherein the top wall 60 of the housing 26 defines a plurality of jagged slots 98, 100, 102, 104, 106 and 108 for accessing more than one valve body rotational position. Movement of handle 80 along individual straight segments of the jagged slots aligns a different lumen with passage 42. The top wall 60 also defines a pair of arcuate slots 110 and 112 for rotating the valve body out of the closed position; it being understood that if the arcuate slots 110 and 112 were straight instead of curved, movement of handle 80 along the slots would merely cause valve body 46 to rotate about the longitudinal axis of the sleeve and would thus keep the solid surface 54 of the valve body centered on the passage 42 thereby maintaining the valve assembly 12 in the closed position.

Figure 12:
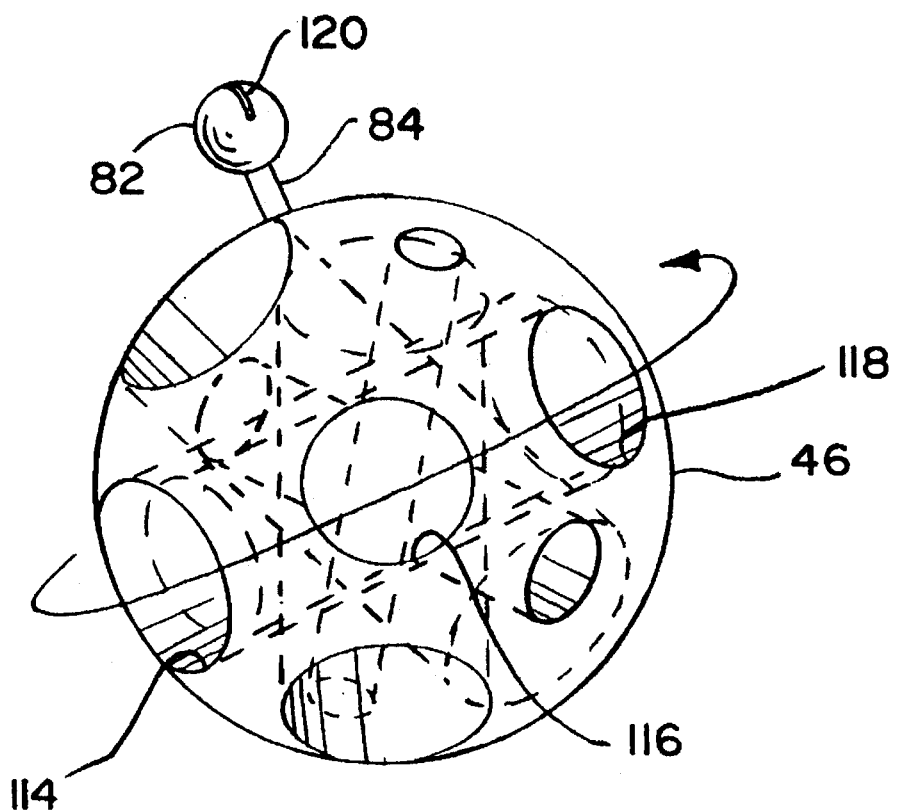
FIG. 12 is an enlarged perspective view of another valve body for use in the endoscopic portal of the present invention.

Further, with handle 80 disposed centrally or within a slotted opening, it is possible to rotate the handle 80 about the longitudinal axis of the shaft 84 to turn the valve body as shown in FIG. 12 to successively align lumens 114, 116 and 118 formed along the rotational path of the body. Hence, the entire surface of the valve body can be utilized for defining lumens except that portion of the sphere used for covering the longitudinal passage 42 in the closed position. Accurate alignment of the lumen with passage 42 when rotation of the handle 80 is permitted, can further be assured by use of indicia 120 on the handle 80 in combination with the indicia 94 on the housing wall 60. If, however, rotation of the handle 80 is not needed or desired, handle 80 can be restrained from rotating by securing the handle shaft 84 to the bias element 86 in such a manner to prevent rotation of the handle 80.

From the above, it will be appreciated that the endoscopic portal of the present invention can be used for engaging medical instruments of various sizes in sealing relation to prevent fluid flow therethrough while allowing the medical instruments to be introduced into an anatomical cavity and removed in succession during a procedure. The valve assembly of the present invention can be used in combination with known flapper valves, elastic seals and the like mounted in the housing to provide added protection against leakage, but is particularly advantageous when used alone in order to reduce the overall size of the portal. The components of the endoscopic portal can be made of any suitable, medical grade materials to permit sterilization for reuse or for single patient use and can be made of multiple parts of various configurations and materials to reduce cost. The valve body can be solid or hollow, spherical, spheroidal or oblate, or any combination thereof, and can be made of separate parts as in a perforated shell surrounding a spherical or non-spherical member such as a tube. The bias member for returning the valve body to the closed position can be an elastic membrane as shown or any other resilient member or mechanism, including helical coil springs, leaf springs, elastic cords and bands or magnets. The valve body can be automatically or manually locked in one or more predetermined positions aligning a lumen with the longitudinal passage by, for example, utilizing detents that engage the body and are released either manually or in response to withdrawal of the medical instrument from the lumen and/or housing.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An endoscopic portal comprising
   a tubular sleeve for insertion through an anatomical cavity wall to provide access within the anatomical cavity for medical instruments, said sleeve having an open distal end adapted to be disposed within the anatomical cavity and an open proximal end adapted to be disposed externally of the anatomical cavity;
   a housing mounting said open proximal end of said sleeve; and
   valve means disposed at said open proximal end of said sleeve for controlling passage of fluids through said sleeve, said valve means including a substantially spherical valve body rotatably mounted in said housing and defining a plurality of lumens of varying size, said lumens being individually alignable with said open proximal end of said sleeve to engage medical instruments therethrough in sealing relation.

2. An endoscopic portal as recited in claim 1 wherein said lumens extend diametrically through said valve body.

3. An endoscopic portal as recited in claim 2 wherein each lumen has a central longitudinal axis and said longitudinal axes of said passages are arranged in multiple planes.

4. An endoscopic portal as recited in claim 1 and further comprising a valve block mounted in said housing and defining a cavity for receiving said valve body.

5. An endoscopic portal as recited in claim 1 wherein said valve body has a closed position blocking communication with said open proximal end of said sleeve.

6. An endoscopic portal as recited in claim 5 wherein a portion of said valve body between said lumens has a surface area to block communication with said open proximal end of said sleeve when said valve body is in said closed position.

7. An endoscopic portal as recited in claim 6 wherein said valve body includes a handle and said housing includes a top wall defining a dome with a plurality of slotted openings formed therein for passage of said handle therethrough, said handle being movable along said slotted openings to rotate said valve body and to selectively align said lumens with said open proximal end of said sleeve.

8. An endoscopic portal as recited in claim 7 and further comprising bias means, coupled with said handle, for biasing said valve body to the closed position.

9. An endoscopic portal as recited in claim 8 wherein said bias means is an elastic membrane.

10. A method of forming a portal in the wall of an anatomical cavity comprising the steps of
    rotating a spherical valve body within a valve housing to selectively align one of a plurality of lumens formed in said valve body with an open proximal end of a portal sleeve mounting said valve housing;
    inserting a penetrating member through said lumen and portal sleeve;
    penetrating the anatomical cavity wall with said penetrating member and said portal sleeve; and
    withdrawing said penetrating member from said sleeve.

11. A method of forming a portal in the wall of an anatomical cavity as recited in claim 10 and further comprising, after said step of withdrawing said penetrating member, biasing said valve body to rotate into a closed position blocking said open proximal end of said portal sleeve.

12. A method of forming a portal in the wall of an anatomical cavity as recited in claim 11 and further comprising, after said step of biasing said valve body to a closed position, rotating said valve body away from said closed position to selectively align one of said plurality of lumens formed in the valve body with said open proximal end of said portal sleeve and inserting a medical instrument through said valve body and portal sleeve to access a site within the anatomical cavity.

13. A method of forming a portal in the wall of an anatomical cavity as recited in claim 11 wherein said step of rotating the valve body includes the step of moving a handle connected with the valve body in at least one of a longitudinal and lateral direction to rotate the sphere.

14. A method of forming a portal in the wall of an anatomical cavity as recited in claim 11 wherein said step of rotating the valve body includes the step of rotating a handle connected with the valve body about a longitudinal axis of the handle.

* * * * *